US006102036A

United States Patent [19]

Slutsky et al.

[11] Patent Number: 6,102,036
[45] Date of Patent: Aug. 15, 2000

[54] BREATH ACTIVATED INHALER

[75] Inventors: Arthur Slutsky, Toronto; Noe Zamel, Willowdale, both of Canada

[73] Assignee: Smoke-Stop, Toronto, Canada

[21] Appl. No.: 09/126,223

[22] Filed: Jul. 30, 1998

Related U.S. Application Data

[63] Continuation of application No. 08/229,505, Apr. 12, 1994, abandoned.

[51] Int. Cl.[7] .......... A61M 15/00

[52] U.S. Cl. .......... 128/203.15; 128/203.12; 128/202.21

[58] Field of Search .......... 128/203.12, 203.15, 128/203.21, 202.21; 131/194, 271, 273

[56] References Cited

U.S. PATENT DOCUMENTS

| | | | |
|---|---|---|---|
| 2,549,303 | 4/1951 | Friden | 128/203.15 |
| 2,579,280 | 12/1951 | Trumbour et al. | 128/203.15 |
| 2,603,215 | 7/1952 | Arnow | 128/203.15 |
| 2,992,645 | 7/1961 | Fowler | 128/208 |
| 3,669,113 | 6/1972 | Altounyan et al. | 128/203.15 |
| 3,679,102 | 7/1972 | Charle et al. | 222/192 |
| 3,831,606 | 8/1974 | Damani | 128/203.15 |
| 3,870,794 | 3/1975 | Hutchinson et al. | 424/264 |
| 4,307,734 | 12/1981 | Blankenship | 128/203.15 |
| 4,524,769 | 6/1985 | Wetterlin | 128/203.15 |
| 4,627,432 | 12/1986 | Newell et al. | 128/203.15 |
| 4,635,651 | 1/1987 | Jacobs | 131/270 |
| 4,655,229 | 4/1987 | Sensabaugh, Jr. et al. | 131/273 |
| 4,811,731 | 3/1989 | Newell et al. | 128/203.15 |
| 4,895,719 | 1/1990 | Radhakrishnan et al. | 424/45 |
| 5,284,133 | 2/1994 | Burns et al. | 128/200.23 |
| 5,441,060 | 8/1995 | Rose et al. | 131/271 |

FOREIGN PATENT DOCUMENTS

| | | |
|---|---|---|
| 946280 | 4/1974 | Canada . |
| 1072569 | 2/1980 | Canada . |
| 1116516 | 1/1982 | Canada . |
| 168921 | 4/1992 | Norway . |
| 1242211 | 8/1971 | United Kingdom . |
| 1520247 | 8/1975 | United Kingdom . |
| 1569611 | 6/1980 | United Kingdom . |
| WO 91/01656 | 2/1991 | WIPO . |

OTHER PUBLICATIONS

Asaro, Danela et al, *The Miconisationof Cosmetic Produts*, Advanced Power Technology & Micoronisation, press release & process update Jan. 1993, Pharmaceutical and Chemical News, Dec. 1992.

Oates and Wood, New Eng. J. Med. 319, 1318, 1988.

Burch et al, Am. Rev. Respir. Di9s. 1989 140:955.

Bell et al, Journal of Pharmaceutical Sciences, vol. 60, No. 10, Oct. 1971.

Newman et al, Eur Resoir J., 1989, 2, 247–251.

Wetterlin, Pharmaceutical Research, vol. 5, No. 8, 1988, 506–508.

Wallace and Lasker, Science, Vo. 260, May 14, 1993, 913.

Tennesen et al, JAMA, Mar. 10, 1993, vol. 269, No. 10, 1268–1271.

Olsson et al, J. Aerosol Sci., vol. 19, No. 7, 1109–1111, 1988.

Presson & Wiren, Eur. Resoir J., 1989, 2, 253–256.

Lichtneckert & Lundgren, Springer–Verlag, 31, 201–204, Mar. 6, 1973.

*Primary Examiner*—Aaron J. Lewis
*Attorney, Agent, or Firm*—Philip C. Mendes da Costa; Bereskin & Parr

[57] ABSTRACT

A method of assisting a person to withdraw from cigarette induced nicotine dependency, comprising introducing a predetermined dose of a non-pressurized, particulate medicament comprising at least one nicotine formulation suitable for absorption into the bloodstream of the person through the alveoli and small airways of the person's lungs into a breath activated inhaler for use by said person as a cigarette substitute. A breath activated inhaler which may be used in accordance with this method is also disclosed.

17 Claims, 4 Drawing Sheets

BREATH ACTIVATED INHALER

This application is a continuation of U.S. patent application Ser. No. 08/229,505, filed Apr. 12, 1994 now abandoned.

FIELD OF THE INVENTION

The present invention relates to a breath activated inhaler for dispensing a medicament into the lung and a method of assisting withdrawal from tobacco induced nicotine dependency by the inhalation of nicotine from a breath activated inhaler. The invention further relates to the use of nicotine inhalers as tobacco substitutes (e.g. cigarette, cigar, pipe).

BACKGROUND OF THE INVENTION

In industrialized countries about one third of the adult population smokes cigarettes, resulting in a major avoidable cause of morbidity and mortality. Smoking is a contributory or causative factor in a number of diseases including respiratory diseases such as emphysema, chronic bronchitis, lung infections, and lung cancer; cardiovascular disease; gastric and duodenal ulcers; and cancer of the lung, oral cavity, larynx and oesophagus.

Most regular smokers become addicted to, or dependent upon, the pharmacological effects of nicotine in tobacco smoke. Nicotine is rapidly absorbed across the blood brain barrier and exerts a direct action on nicotine receptors in the spinal cord, autonomic ganglia and adrenal medulla. For more detailed information on the pharmacologic effects of nicotine see, for example, Oates and Wood, New Eng. J. Med. 319:1318, 1988. Nicotine itself has been implicated as a contributory factor in coronary heart diseases, peripheral vascular disease and hypertension.

Although nicotine is responsible for the addictive nature of cigarette smoking, most of the harmful health effects of smoking are attributable to other constituents in cigarette smoke (The Lancet, 337:1191, May 18, 1991). The combustion of tobacco in cigarettes results in the production of up to 4,000 compounds and the inhalation of such unwanted by-products as tar, combustion gases and a range of carcinogens. Nicotine may be nitrosated to form highly carcinogenic tobacco-specific N-nitrosamines in tobacco smoke, or in the cured smokeless tobacco for use as chewing tobacco or snuff. It is an unfortunate feature of cigarette smoking that the negative consequences of nicotine addiction are largely manifested by the inhalation of toxic and carcinogenic materials generated by the combustion of tobacco.

Addiction to smoking is based upon a pharmacological dependence on nicotine, an addiction comparable to that arising from the use of heroin. There are a number of acute symptoms of smoking cessation relating to nicotine withdrawal including irritability, anxiety, insomnia and a craving for nicotine. The addictive nature of nicotine poses a major obstacle to those who wish to quit smoking and a number of approaches have been developed to aid individuals in their efforts to stop smoking. The more successful of these involve therapy with nicotine substitutes such as chewing gum, nicotine patches, nicotine nasal sprays, nicotine vapour and the like. However, as discussed in more detail below, these approaches have met with limited user acceptance and limited success. In addition, there are individuals who are unable to stop despite repeated attempts, due to the addictive nature of nicotine. These individuals could benefit from a product which fulfilled their craving for nicotine, but did not have the same detrimental health consequences as cigarettes.

Smoking is a uniquely effective form of systemic drug administration. As nicotine enters the circulation via the pulmonary circulation, it is speedily transported to the brain. Smokers achieve a rapid peak in nicotine levels in the blood within one or two minutes after finishing a cigarette. Nicotine substitutes generally contain nicotine in solid form, in a vapour or in solution. As nicotine is a base, these preparations are alkaline. The alkalinity of nicotine substitutes is frequently increased, for example to Ph 10 because at high Ph nicotine is not ionized and ionization is know to impede the passage of nicotine across biological membranes (Burch et al., Am. Rev. Respir. Dis. 1989, 140:955).

With respect to nicotine gum, it is known that nicotine, even at an alkaline Ph, is absorbed slowly across the mucous membranes of the oral cavity, so absorption by this route does not produce the very rapid increase in nicotine levels associated with cigarette smoking. Therefore, buccal absorption has proved to have limited use in simulating the effects of cigarette smoking and lessening the adverse symptoms of nicotine withdrawal. Lower nicotine levels are achieved from chewing nicotine gum compared to smoking cigarettes and the gum has been associated with gastro intestinal side effects, hiccups, mouth ulcers and sore throat. The amount of nicotine absorbed is also highly variable and is dependent upon the chewing and swallowing actions of the user over a prolonged period of time.

Nicotine patches are associated with skin irritation at the application site. Both nicotine gum and dermal patches result in slow absorption of nicotine which is frequently not effective in satisfying the patient's craving for cigarettes. This may be one of the reasons for the lack of success of these forms of therapy in weaning subjects from smoking.

Self-propelled aerosols (also know as "pressurized aerosols") which contain nicotine in solution have also been proposed as cigarette substitutes. An example is the self-propelled aerosol formulation of Jacobs in U.S. Pat. No. 4,635,651. Such formulations are packaged in pressurized metered dose delivery systems. As shown in Jacobs, these delivery systems contain a water based aerosol formulation and a propellant such as pressurized freon which are stored in a pressurized storage container. When the device is used by an individual, the user aims the delivery system into their mouth. The user then inhales while causing a premetered dose of aerosol to be forced from the storage container and expelled at high speed into the user's mouth.

There are a number of problems with such pressurized aerosols. Pressurized aerosols require coordination on the part of the user who ideally should inhale at exactly the same time as the device is actuated in order to deliver the drug into the lungs. Frequently pressurized aerosols are inhaled near the end of respiratory intake resulting in poor delivery to the distal portions of the lungs. For the foregoing reason, the dose of nicotine administered by using pressurized aerosols can not be accurately controlled.

Failure to coordinate actuation of an aerosol inhaler and inhalation results in deposition of the aerosol in the oral cavities and upper respiratory tracts. In addition, even if the user properly aims the delivery device and coordinates the inhalation, the speed with which the aerosol is expelled from the device and enters the mouth causes much of the aerosol to impact on the throat and upper airways of the user. For example, Jacobs in U.S. Pat. No. 4,635,651 expelled particles of about 40 $\mu$m. These particles would comprise agglomerations of particles and solvents. As the particles travel from the inhaler into the airway of the user, the particles would break up into smaller particles and some of the solvent would operate. However, even these smaller particles would still be at least about 10 μm as they travelled through the mouth of the user and would accordingly impact on the throat and upper airways of the user. Aerosols utilize nicotine which is in solution. Since nicotine in solution has an alkaline pH which irritates the throat and upper airways, aerosols have poor acceptance by smokers (Burch et al., 1989, Am. Rev. Respir. Dis. 140:955).

Further, it is problematic to produce particles of an optimal size for absorption in the alveoli with a self-propelled aerosol. Jacobs in U.S. Pat. No. 4,635,651 included a solid particulate component of defined size into a pressurized aerosol formulation of an inhalable nicotine solution.

SUMMARY OF THE INVENTION

It has been determined that a controlled dose of a medicament suitable for absorption into the blood stream of a patient through alveoli and small airways of the lungs can be delivered to the alveoli and small airways of the patient's lungs by a breath activated powder inhaler while causing only minimal noticeable irritation to the throat and upper airways of the patient and, preferably without causing any noticeable or significant irritation.

It has also been determined that a controlled dose of a medicament containing a pharmaceutically acceptable nicotine preparation suitable for absorption into the bloodstream of the patient through the alveoli and small airways of the lungs can be delivered into the alveoli and small airways of a patient's lungs by a breath activated powder inhaler to mimic the pharmacologic effects of the nicotine administered by a cigarette, cigar, pipe or the like (hereinafter generally referred to as "cigarette") while minimizing or preventing the delivery of extraneous irritants or toxins into the oral cavity and respiratory airways.

The present invention relates to a breath activated nicotine inhaler for use by a patient to introduce a medicament into the patient's lungs, comprising a housing, an air conduit within the housing adapted to conduct air flow to the patient, a non-pressurized, particulate medicament comprising at least one pharmaceutically acceptable nicotine preparation suitable for absorption into the bloodstream of the patient through the alveoli and small airways of the patient's lungs and means for introducing a predetermined dose of said medicament into said air conduit, whereby on activation of said inhaler and inhalation by the patient, the medicament is introduced to the patient's lungs.

The predetermined dose of nicotine may be from about 0.1 to about 10 mg and preferably from about 0.2 to about 2 mg of nicotine. In order to more closely mimic the pharmacologic effects of the nicotine administered by a cigarette, the inhaler may be adapted to provide a series of small doses of the nicotine preparation, such as from about 0.1 mg. to about 0.5 mg., over the period of time in which an individual would smoke a cigarette.

In an embodiment of the invention, the medicament may additionally comprise a pharmaceutically acceptable carrier, binder, excipient, surface active agent, diluent, or a combination thereof.

In a further embodiment of the invention, the breath activated nicotine inhaler may have a resistor adapted to impart resistance to the flow of air in the air conduit.

The nicotine may be a nicotine salt such as a sulphate or a bitartrate or a nicotine base, such as a nicotine oil formulation or mixtures thereof. These nicotine formulations may be absorbed, adsorbed or aggregated onto a suitable carrier or excipient. Alternately, the nicotine oil formulation may be encapsulated.

The invention also relates to a method of assisting a person to withdraw from cigarette induced nicotine dependency comprising introducing a predetermined dose of a non-pressurized, particulate medicament comprising at least one nicotine formulation suitable for absorption into the bloodstream of the person through the alveoli and small airways of the person's lungs into a breath activated inhaler for use by said person as a cigarette substitute.

The invention further relates to a method of assisting withdrawal from cigarette induced nicotine dependency comprising providing a breath activated nicotine inhaler comprising a housing; an air conduit within the housing adapted to conduct air flow to a patient, a particulate medicament comprising at least one pharmaceutically acceptable nicotine formulation suitable for absorption into the bloodstream of the person through the alveoli and small airways of the person's lungs; and, means for introducing the medicament into said air conduit. The method further comprises introducing a predetermined dose of medicament into the air conduit; applying the patient's mouth to one end of the air conduit and; inhaling air through the air conduit, thereby drawing medicament into the lungs, preferably the distal region of the lungs.

In a preferred embodiment the method is repeated at time intervals sufficient to reduce the negative effects of nicotine withdrawal. In a further preferred embodiment, where a patient appears to be unable to stop smoking, the breath activated inhaler may be used as a cigarette substitute.

In another aspect, the invention relates to a breath activated inhaler for use by a patient to introduce a medicament into the patient's lungs, comprising:

a housing having a first opening and a second opening, said first opening and said second opening being releasably sealed, one of said first opening and said second opening being adapted to deliver the medicament to the mouth of the patient; and, a non-pressurized, particulate medicament suitable for absorption into the bloodstream of the patient through the alveoli and small airways of the patient's lungs positioned in said housing, whereby, when said seals are removed from said first opening and said second opening, said housing and said openings define an air conduit adapted to conduct air flow to the patient; and, on inhalation by the patient, the medicament is introduced to the patient's lungs.

The breath activated inhaler according to this aspect of the invention may contain a single dose of a medicament which is intended to be inhaled by the patient in a single breath. Alternately, if the dosage which is required by a patient is sufficiently great that it would cause irritation to the throat and upper airways of the patient, a full dose may be located in the inhaler and the inhaler is preferably provided with by-pass air feed means for supplying air to dilute the air passing through said housing so as to reduce the concentration of the medicament in the air which is inhaled by the patient.

Preferably, the by-pass air feed means is located near the opening which is adapted to deliver the medicament to the mouth of the patient.

In a further aspect, this invention also relates to a method of introducing a medicament into the lungs of a patient using a breath activated inhaler having a housing having a first opening and a second opening, said first opening and said second opening being releasably sealed, one of said first opening and said second opening being adapted to deliver the medicament to the mouth of the patient; and, a non-pressurized, particulate medicament suitable for absorption into the bloodstream of the patient through the alveoli and small airways of the patient's lungs positioned in said housing, said method comprising the steps of:

(a) agitating said medicament in said housing to disperse said medicament throughout said housing;

(b) releasing said seals on said first and second openings; and (c) inhaling said medicament.

In these latter two embodiments, the housing is preferably under sub-atmospheric pressure. The housing has one opening which is adapted to be received in the mouth of a patient. In use, the medicament in the housing is agitated so as to disburse the medicament throughout the housing. This may be achieved by the patient releasing the seal on one opening of the housing. Since the housing is at sub-atmospheric pressure, the release of the seal will cause air to rapidly enter the chamber and disburse the medicament throughout the housing. The patient may then release the seal on the other opening of the housing and inhale in a slow and controlled manner so as to draw all of the medicament into the patient's lungs.

In a further aspect of this invention, a method of manufacturing a breath activated inhaler is disclosed. The breath activated inhaler is used by a patient to introduce a medicament into the patient's lungs. The inhaler has a housing with a first opening and a second opening, one of said first opening and said second opening being adapted to deliver the medicament to the mouth of the patient. The method of manufacturing the inhaler comprises the steps of:

(a) placing said housing between first and second filter means;

(b) passing a fluid containing entrained medicament through said first filter means and said second filter means, to deposit said medicament in said housing; and (c) sealing said first and said second openings, said first filter means being adapted to remove from said fluid particles of the medicament which are sufficiently large to irritate the throat and upper airways of the patient, said second filter means being adapted to pass theretrough said fluid and particles which are sufficiently small that they would not be absorbed in the lungs of the patient.

BRIEF DESCRIPTION OF THE DRAWINGS

This and other advantages of the instant invention will be more fully and completely understood by reference to the following description of the following drawings of an exemplary embodiment of the invention in which.

DETAILED DESCRIPTION OF THE INVENTION

As hereinbefore mentioned the present invention relates to a breath activated nicotine inhaler for dispensing a medicament such as a nicotine formulation to the large airways as well as the distal regions of the lung, and in particular, the alveoli and the small airways. In the art, "small airways" is used to refer to the passages in the lungs which are less than about 2 mm in diameter. The breath activated inhalers of the invention deliver a predetermined dose of medicament such as nicotine into the alveoli and small airways, in a particulate form which is sized for rapid absorption and which simulates the pharmacologic effect of a rapid increase in nicotine blood levels similar to that achieved by cigarette smoking. The rapid nicotine absorption is due to deposition of nicotine in the airways and alveoli of the lung where medicaments are absorbed efficiently across the large surface area of the highly vascularized alveoli and small airways.

Breath activated inhalers having a housing, an air conduit adapted to conduct air flow to a patient, and means for introducing a medicament into the air conduit are generally known in the art, see, for example, U.S. patent Ser. No. 4,524,769 to Wetterlin; Bell et al., J. Pharmaceut. Sci. 60:1559, 1971 and; Newman et al., Eur. Res. J. 2:247, 1989. Examples of suitable inhalers include SPINHALER®, TURBUHALER® AND ROTAHALER® brand inhalers. Breath activated inhalers differ from pressurized aerosol inhalers in that breath activated inhalers are activated by inhalation of the user so that the medicament is reliably drawn into the distal regions of the lung.

Figure 1:
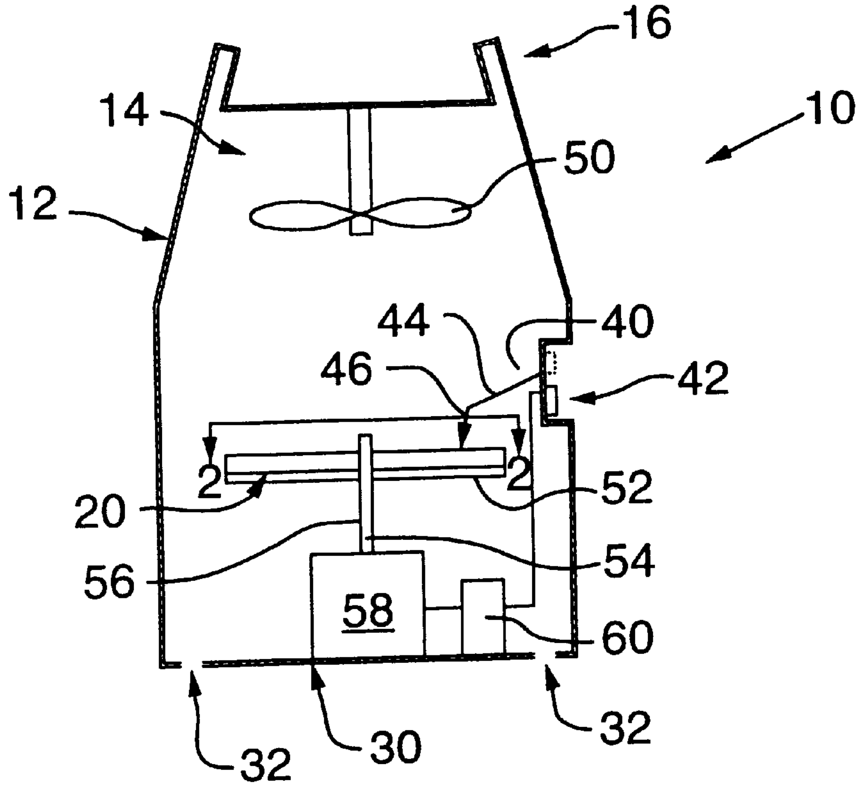
FIG. 1 is a cross-section of an inhaler according to the instant invention.
Figure 2:
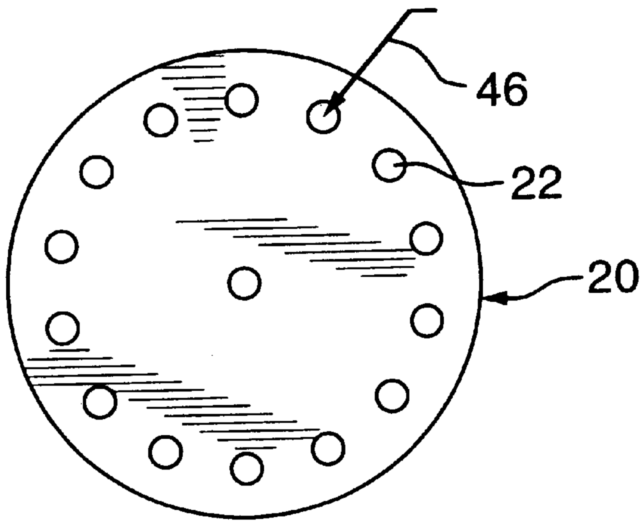
FIG. 2 is a top plane view along the line 2—2 in FIG. 1.

As shown in FIG. 1, breath activated inhalers (10) generally comprise a hollow housing (12) with an air conduit (14). One end of the air conduit (16) is adapted for insertion into the mouth of a patient. Such inhalers have means for introducing the medicament into the air conduit, for example a rotatable disc (20) having spaced containers (22) of medicament which can be rotated to introduce a single dose of medicament into the air conduit (see FIG. 2). Referring to FIG. 1 in more detail, housing (12) has a bottom surface (30). Bottom surface (30) is provided with air inlets (32). Air inlets (32) are sized to provide an appropriate amount of air into inhaler (10). As the air enters inhaler (10), it travels past rotatable disc (20) and exits through end (16). In use, the patient inserts one end of the air conduit into their mouth and inhales. The turbulent airstream created in the air conduit by the patient's inspiration fluidizes the medicament to produce a cloud of medicament particles which are carried into the lung with the inhaled air.

Inhaler (10) also includes means (40) for opening spaced containers (22) in a controlled fashion. As shown in FIG. 1, inhaler (10) includes actuator button (42). Button (42) is movable between a first position as shown in FIG. 1 and a second position which is shown in dotted outline in FIG. 1. Button (42) is connected to extender arm (44). Attached to the distal end of extender arm (44) is piercing member (46). Piercing member (46) has a sharpened edge so that, when actuated, it will pierce spaced container (22) thus opening the container and allowing the medicament to be fluidized by the passage of air over the disc. Extender arm (44) and piercing member (46) are configured such that the sharpened edge of piercing member (46) is positioned adjacent the circle defined by spaced containers (22). When actuator button (42) is moved to the position shown in dotted outline, piercing member (46) is moved so as to open spaced container (22).

The breath activated nicotine inhaler of the invention provides a pre-determined dose of a medicament such as nicotine to the lung. The dose should be physiologically acceptable for administration to humans by this route of administration. The dose of nicotine delivered to the lungs may be from about 0.1 to about 10 mg, preferably from about 0.2 to about 3 mg, more preferably from about 0.2 to about 2 mg, and most preferably about 1 mg as a total dose in any one treatment. However, one treatment may consist of multiple inhalations of a smaller dose over a period of time thus more closely simulating the act of smoking and minimizing the irritant effect of nicotine impaction in the mouth and throat. Accordingly, in order to more closely mimic the pharmacologic effects of the nicotine administered by a cigarette, the inhaler may be adapted to provide a series of small doses of the nicotine preparation, such as from about 0.1 mg. to about 0.5 mg., over the period of time in which an individual would smoke a cigarette, typically from about 1 to about 10 minutes.

Most inhalers currently in use for the treatment of respiratory disorders use a low resistance so that sufficient air flow can be generated by persons having impeded respiratory capacity and obstructed airways, resulting, for example, from asthmatic attack. However, the high flow rates generated by users not having obstructed airways could cause the fine particles of the medicament to impact against the back of the upper airway. Accordingly, one embodiment of the present invention provides an inhalation device with a resistor which may serve two functions. First, to restrict the cross-sectional area of the air conduit so as to reduce the flow rate of air thereby decreasing impaction at the back of the throat. Secondly, to produce turbulence in the air flow to break up any aggregate particles of the medicament which may be present in the inhaler prior to inhalation. For example, as shown in FIG. 1, inhaler (10) may be provided with rotating means (50) which is mounted at end (16). Air passing by rotating means (50) is disrupted so that aggregate particles of the medicament which might be formed are disrupted.

To avoid the nicotine in the medicament from impacting on the throat and upper airways of the user during inhalation, the medicament preferably enters the mouth of the user with a momentum sufficiently low to cause the medicament to be entrained in the air of the inhalation so as to follow the curvature in the pathways of the upper respiratory tract and be carried to the lungs of the user. To achieve this result, the mass of the particles of the medicament and the velocity of the medicament must be in a defined range.

The nicotine should be present as a stable powder in a size range suitable for deposition on and absorption across the small airways and the alveolar lining taking into account the amount of water which may be absorbed by the particles as they pass through the lungs. Larger particles, over 5 μm tend to be deposited in the oral cavity and upper airways, whereas small particles under 0.5 μm tend to be exhaled from the lung without deposition. The particles grow in size as they are exposed to water in the atmosphere and in the airways of the user. For example, a 0.1 μm particle may increase to about 0.5 μm as it passes through the airways to the alveoli and smaller airways of a user. In order to have an appropriate mass, the individual medicament particles, when they exit from the inhaler, may vary in size from about 0.1 μm to about 5, preferably from about 0.1 μm to about 3 μm, more preferably from about 0.1 μm to about 2 μm and most preferably from about 0.1 μm to about 1 μm. However, it should be noted that the individual particles in the medicament introduced into the inhaler may be aggregated into larger aggregates which are subsequently broken down in the turbulent air flow on inspiration.

To have an appropriate velocity, the air conduit of the inhaler is sized to permit an air flow rate therethrough of up to about 1.0 L/s, and preferably up to about 0.5 L/s upon inhalation by the patient.

As discussed above, the use of the instant invention allows a patient to achieve a rapid increase in nicotine blood level which effectively simulates cigarette smoking. It is recognized that the amount of nicotine which may be imparted to an individual may reach toxic proportions if the individual administers doses of the medicament too frequently. Accordingly, it is preferred to include means to limit the frequency with which inhaler (10) may be utilized. For example, as shown in FIG. 1, rotatable disc (20) may be mounted on plate (52) which is attached to axle (54). Axle (54) has one end (56) which is attached to electric motor (58) powered by a battery (not shown). Rotation of motor (58) causes axle (54) to rotate thus rotating rotatable disc (20). Motor (58) is calibrated so that each activation of motor (58) causes rotatable disc (20) to move a sufficient distance to place a new spaced container (22) adjacent piercing means (46). Actuator button (42) is connected to timing means (60). Accordingly, when a patient utilizes inhaler (10), button (42) is moved to the position shown in dotted outline in FIG. 1.

If the amount of nicotine contained in a single dose is designed to simulate an entire cigarette, then timer (60) may be preset so as to allow a further dose to be taken only after a reasonable period of time (e.g. 20 to 30 minutes) has elapsed. Timer (60) is conventional and is connected to and actuated when button (42) is pushed. Timer (60) cuts off power to motor (58), for example, two seconds after button (42) is pushed (to allow the motor enough time to advance disc (20) by one step) and keeps the power to motor (58) cut off until timer (60) has counted down the desired time (which can be made adjustable).

If each nicotine dose is made equivalent only to that obtained by one or two puffs from a cigarette, then timer (60) would normally not be needed. However, if desired, timer (60) may be preset to allow a plurality of doses to be taken over a relatively short period of time to simulate the nicotine levels which are achieved when an individual smokes a cigarette. For example, timer (60) could be provided and set to permit a desired number of doses (puffs) within a preset time (for example 5 to 10 doses within, for example, ten to fifteen minutes), and then to cut off power to motor (58) until a selected time interval (e.g 20 to 30 minutes) has elapsed. By adjusting the number of doses allowed in each period and the time intervals between the periods, the total nicotine dosage can be controlled and, if desired, gradually reduced to wean the patient from his/her nicotine additions.

Alternatively, timer (60) can be set simply to count the time between doses even when one dose simply simulates one or two puffs on a cigarette.

The breath activated nicotine inhalers of the invention are characterized in that the medicament to be drawn into the lungs may comprise one or more nicotine formulations. The present invention provides a powdered medicament comprising nicotine for use in a breath activated powder inhaler. The nicotine may be a nicotine salt such as a sulphate or a bitartrate or a nicotine base, such as a nicotine oil formulation or pharmacologically active analogues or derivatives of nicotine or substances which mimic the effects of nicotine, either alone or in combination with other active substances. The medicament may be discrete particles or it may be absorbed, adsorbed or aggregated onto a suitable carrier or excipient. Alternately, if the medicament is a liquid, such as a nicotine oil formulation, the medicament may be encapsulated.

Nicotine is known to form salts with almost any acid and double salts with many metals and acids. Nicotine salts vary in their ability to absorb water. It has been found that the ability of nicotine salts to penetrate into the distal regions of the lung, such as the peripheral airways and the alveoli, is based in part upon the size of the particles of the medicament and the degree of hygroscopicity of the medicament. For example, some nicotine salts are very hygroscopic. Accordingly, the particles rapidly increase in size when exposed to an airway of the patient which is fully water saturated. The absorption of water by the particles favours the deposition of the nicotine particles in the central airways of the respiratory system as opposed to the peripheral regions of the lung. By selecting a nicotine salt which is somewhat hygroscopic, and selecting the particles so as to be capable of being inhaled and transported to the alveoli and small airways, a rapid increase in the blood level of nicotine may be obtained in a patient. This rapid increase in blood level simulates cigarette smoking. Accordingly, the nicotine may be selected, based upon its hygroscopicity, to provide nicotine salt particles which are of the sufficient size to be transported to the distal regions of the lungs and, in particular, to the alveoli and small airways. Preferred nicotine salts include sulphate and tartrate, chloride, bi-chloride, bitartrate, picrates, aipricrates, salicylates, picrolonates and dipicrolonates. More preferably, the salt is sulphate, bitartrate or mixtures thereof.

A medicament such as nicotine may be mixed with one or more pharmacologically acceptable binders, excipient or diluents, surface active agents, colouring or flavouring agents, suitable for inhalation. Examples of suitable solid diluents or carriers which may be used in the medicament include mannitol, dextrose and lactose.

In order to facilitate storage, handling and introduction of the medicament into the air conduit the medicament may be packaged in powdered form with a desiccant to prevent moisture absorption.

The medicament of the invention, if ionized (e.g. a nicotine salt), is poorly absorbed across the mucosa of the upper airways and is relatively non toxic to those surfaces. Surprisingly, the extensive cross-sectional area of the small airways and the alveolar lining provides a large stable buffering environment for the ionized nicotine. As the nicotine is buffered in the lungs, the pH of the nicotine increases and the nicotine changes to a non-ionized form which may be readily transported across the biological membranes in the lung. Thus, nicotine, whether acidic or basic, delivered into the distal regions of the lung is readily buffered and absorbed by the extensive airway and alveolar surfaces. It is the rapid and efficient absorption across the expansive buffered alveolar and airway surfaces which results in the steep rise in nicotine blood levels mimicking the pharmacological effect of cigarettes. The selective delivery to, and absorption across, the distal lung regions therefore mimics the pharmacologic effects of cigarette-derived nicotine while decreasing or eliminating the undesirable side effects of smoking or other nicotine substitution therapies.

The medicaments of the present invention are intended for administration to humans and preferably contain from about 0.1 mg. to about 10 mg. of nicotine. The medicament can be prepared by known methods for the preparation of pharmaceutically acceptable compositions which can be administered to the airways of patients such that an effective quantity of nicotine is provided, which may be combined in a mixture with a pharmaceutically acceptable vehicle as hereinbefore mentioned.

In accordance with one embodiment of the invention a method of assisting a person withdraw from cigarette induced nicotine dependency is provided. The method comprises introducing a medicament comprising one or more nicotine formulations suitable for absorption into the bloodstream of the person through the alveoli and airways of the person's lungs into a breath activated powder inhaler for use by a person as a cigarette substitute.

When smokers attempt to stop smoking the recidivism rate is high due to the negative symptoms of withdrawal from nicotine addiction. Replacement therapy with cigarette substitutes is designed to lessen the impact of nicotine withdrawal and to assist a person in withdrawing from cigarette induced nicotine dependency. Cigarette substitutes are suggested as a replacement for cigarettes during the withdrawal period. The optimal replacement therapy will involve reproducing the sharp increase in nicotine levels achieved by cigarette smoking in order to effectively suppress the withdrawal symptoms. Successful withdrawal from smoking may require the use of the breath activated inhalers of the invention over a period of time during which inhalers are used to deliver successively smaller nicotine doses until complete withdrawal may be effected.

In order to effect a controlled withdrawal from nicotine the present invention provides a breath activated nicotine inhaler to deliver a predetermined dose into the distal regions of the lung. The predetermined dose is introduced into the air conduit from where it is efficiently drawn deep into the lungs. The size of each individual dose may therefore be accurately controlled.

In a preferred embodiment the minimum time interval between doses is also controlled to prevent the patient from receiving an overdose of nicotine. The timer may be set to enforce time periods of from 5 minutes to about 2 hours. If the dosage is set to represent a puff of a cigarette, then the timer may have a first setting to permit several dosages to be taken over a period of a few minutes and a second setting to prevent a second plurality of dosages being taken before the expiry of from 5 minutes to about 2 hours. Accordingly, the present invention provides a highly controlled yet flexible method of assisting a person to withdraw from cigarette-induced nicotine dependency by providing controlled doses of nicotine having a pharmacologic effect similar to that of cigarette smoke without the adverse side effects. The act of inhaling from a device in the mouth may also provide patients with a short-term behaviour substitute for inhaling a cigarette. In some cases where a person is unable to stop smoking, then the inhaler may be used as a replacement for cigarettes.

Figure 3A:
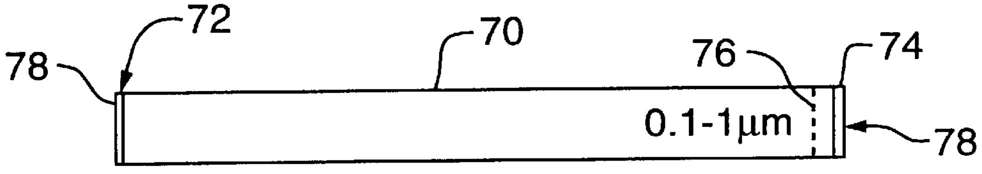
FIG. 3A discloses a cross-section of a further inhaler according to the instant invention.

An alternate inhaler for delivering a medicament to the lungs of a user is shown in FIG. 3A. Inhaler (70) may comprises a longitudinally extending housing having a first end (72) and a second end (74). As will become more apparent below, inhaler (70) may also include filter (76). A stopper (78) is positioned in each of ends (72) and (74).

Inhaler (70) may be of any particular shape. As shown in FIG. 3A, the inhaler may comprises a longitudinally extending cylinder so as to simulate the shape of a cigarette. One of ends (72) and (74) is adapted to deliver a medicament to the mouth of a patient. The other of ends (72) and (74) may be of any particular shape.

Inhaler (70) is preferably manufactured from an air impervious or air impregnable material. Preferably, inhaler (70) is also made from a material which would be effectively electrostatically neutral to the medicament which is placed in inhaler (70). The material may be selected from those which will not develop an electrostatic charge which would attract the medicament particles. For example, inhaler (70) may be manufactured from nylon. Alternately, an electrostatically neutral liner or coating may be placed in inhaler (70). In addition, stoppers (78) are also preferably made of an air impervious or air impregnable material and form a airtight seal with ends (72) and (74). Accordingly, when manufactured, the inhaler has a stable internal environment which is not in air flow communication with the surrounding air.

A particulate medicament suitable for absorption into the bloodstream of a patient through the lungs of the patient and, preferably, through the alveoli and small airway of the patient's lungs, is positioned within the inhaler (70). The medicament may be a nicotine formulation of the particle size discussed above. Preferably, the individual medicament particles may vary in size from about 0.1 μm to about 2 μm and, more preferably, from about 0.1 μm to about 1 μm.

Figure 3B:
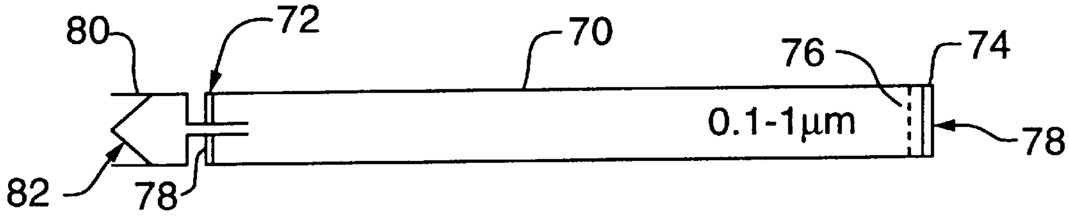
FIGS. 3B and 3C disclose methods of how the inhaler shown in FIG. 3A may be utilized by a patient; and, FIGS. 4A–4D show a method by which a further inhaler according to the instant invention may be manufactured.
Figure 3C:
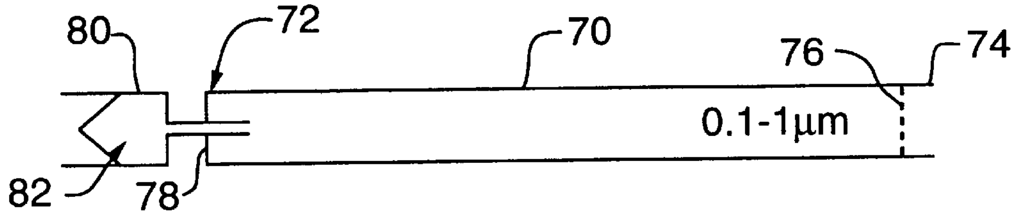

FIGS. 3B and 3C show a method for the use of inhaler (70). As shown in FIG. 3B, mouth end piece (80) may be inserted through stopper (78) at end (72) of inhaler (70). For example, stopper (78) may be a thin walled plastic or rubber member which may be punctured by mouth end piece (80). Accordingly, end (72) of inhaler (70) may itself be sized or adapted so as to be received in the mouth of a patient or may be adapted to receive mouth end piece (80). Mouth end piece (80) may include one way valve (82).

Once mouth end piece (80) is inserted through stopper (78) at end (72) of inhaler (70), stopper (78) may be removed from end (74). Accordingly, end (74), inhaler (70) and mouth end piece (80) define an air conduit. When the patient inhales, the medicament contained in housing (70) is transported through mouth end piece (80), through one way valve (82) and into the lungs of the patient. Preferably, the air conduit is sized so as to permit an air flow rate therethrough of up to about 1 L/s upon inhalation by the patient and, preferably, the airflow rate is up to about 0.5 L/s.

Figure 4A:
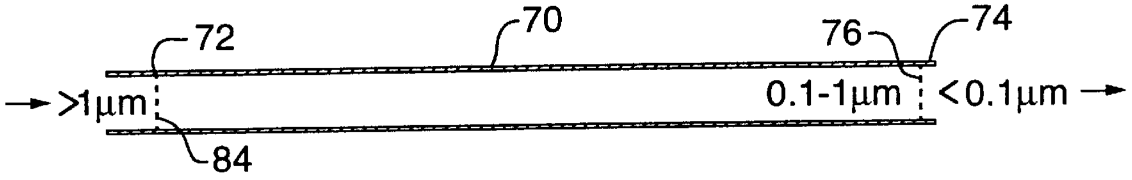

The inhaler may be manufactured by the steps shown in FIGS. 4A–4D. As shown in FIG. 4A, inhaler (70) commences as an longitudinally extending member. Filter (76) is positioned at one end of inhaler (70) and filter (84) is provided at the other end of inhaler (70). Preferably, the filters and in particular filter (76) is made from an electrostatically neutral material such as nylon. Filter (84) is sized so as to prevent large particles which may irritate the throat and upper airways from entering inhaler (70). Filter (76) is sized so as to allow minute particles which would be expelled from the lung of the patient to exit therethrough while retraining in tube (70) those particles of a sufficient size which would be capable of being absorbed in the lungs of the patient. Filter (84) may be sized so as to allow therethrough particles less than 5 μm, preferably less than about 3 μm, more preferably less than about 2 μm and, most preferably less than about 1 μm. Filter (76) may permit particles less than about 0.1 μm from passing therethrough. Accordingly, when air containing a medicament travels in the direction of the arrow shown in FIG. 4A from end (72) to end (74), the larger particles will not enter inhaler (70) and particles which are too small to be retained in the lungs of a patient pass completely through inhaler (70). Thus, the particles which are retained in inhaler (70) may conform to the dimension of particles contained in ordinary cigarette smoke (for example 0.1–2 μm or more preferably 0.1–1 μm).

Figure 4B:
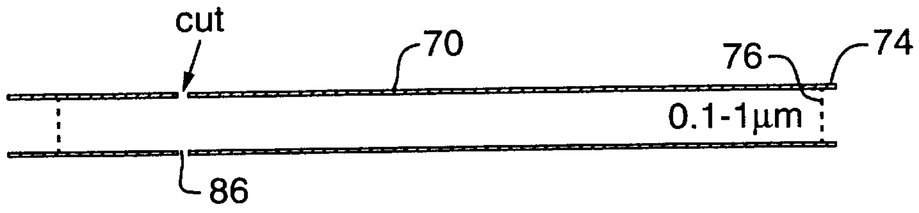
Figure 4C:
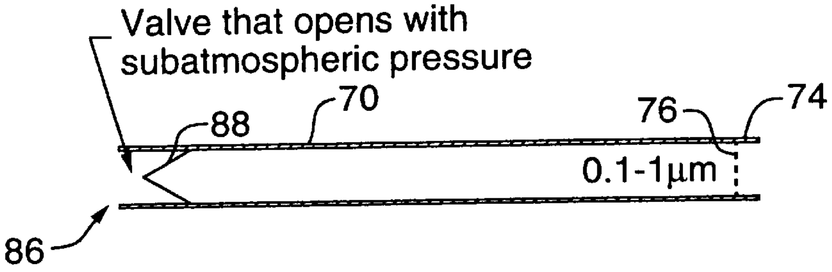
Figure 4D:
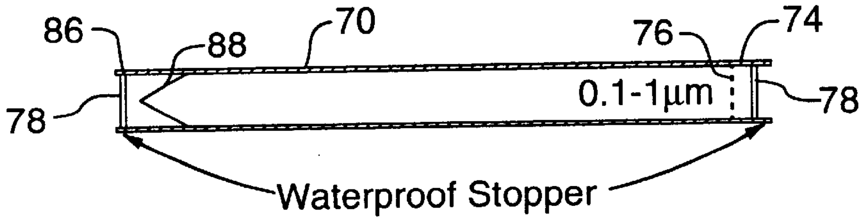

A sufficient amount of air is passed through filter (72) and (74) to insert a predetermined dosage of medicament in inhaler (70). The dosage inserted into inhaler (70) may be determined based upon the concentration of medicament in the air flow and the particle size range contained in the medicament. The medicament will tend to accumulate around filter (76). Once the predetermined dose of medicament is inserted into inhaler (70), filter (84) may be removed from inhaler (70) by cutting inhaler (70) at point (86) as shown in FIG. 4B. As shown in FIG. 4C, one way valve (88) may then be inserted at cut end (86) of inhaler (70). Stoppers (78) may then be inserted in ends (86) and (74).

In an alternate embodiment, the step shown in FIG. 4C may be omitted and a stopper may be placed in end (86) without installing a one way valve (88). According to this embodiment, the inhaler shown in FIG. 3A may be prepared. In another embodiment (not shown) Filter (84) may be part of the machine which injects medicament into inhaler (70). According to this embodiment, the machine would contain an injector (not shown) containing filter (84). The injector would be sized so as to prevent air flowing out end (72) of inhaler (70) thus forcing all of the air and entrained medicament to enter inhaler (70).

When stoppers (78) are removed, and the patient inhales, inhalation will cause the medicament to exit the inhaler and enter the airways of the patient. The medicament may have a tendency to stick to the inner walls of inhaler (70) and to filter (76). Accordingly, a rapid inhalation may be required and this may cause an undesirable amount of medicament to impact upon the throat and upper airways of the patient. According to a preferred embodiment of the instant invention, the medicament in inhaler (70) is agitated prior to inhalation so as to cause the medicament to draw away from the walls of inhaler (70) and filter (76). This may be achieved by the patient shaking inhaler (70) prior to removing stopper (78) and inhaling. Alternately, the medicament in inhaler (70) may be at sub-atmospheric pressure. When one of stoppers (78) is removed, and preferably stopper (78) located at end (74), the in rush of air will cause the medicament to fill inhaler (70). Accordingly, when the other stopper (78) is removed, the patient may inhale in a controlled, slow manner so as to draw all of the medicament into the lungs of the patient.

Inhaler (70) may be used with any particular medicament, including a nicotine compound as discussed herein. Inhaler (70) provides a simple method of providing a controlled dose of a medicament into the alveoli and small airways of the patient's lung without any significant deposition of same in the throat and upper airways which may result in irritation of the throat and upper airways and a reduction in the amount of medicament which is actually absorbed into the bloodstream of the patient.

Due to the design of inhaler (70) a relatively large dose of medicament may be placed in inhaler (70). Due to the low momentum which is imparted to the medicament as it leaves inhaler (70) and enters the patient's mouth, a large dose of medicament may be inhaled in a single breath. Depending upon the medicament and the dosage which may be required, it is appreciated that it may not be possible, even with the use of inhaler (70) for a patient to inhale a full dosage without causing some irritation to the patient's throat and upper airways. If the amount of the dosage is sufficiently high, then two or more inhalers (70) may be utilized by the patient to achieve a full dose.

Figure 5A:
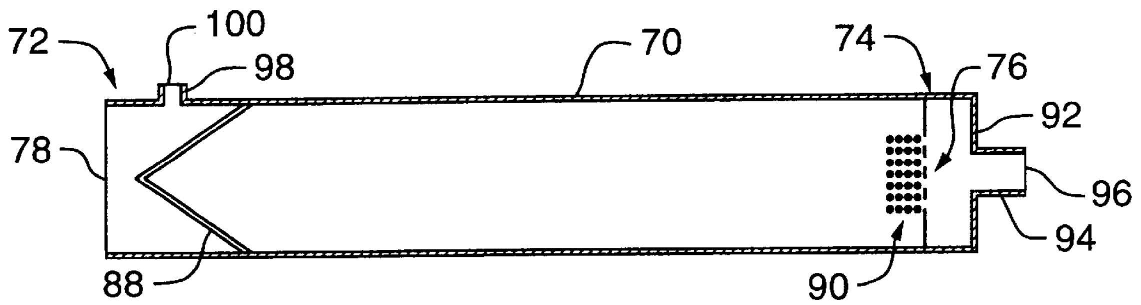
FIGS. 5A–5D show a further embodiment of the inhaler according to the instant invention and the method of use of this further embodiment of the inhaler.

Alternately, inhaler (70) may be designed to contain a full dose of medicament but, due to the use of dilution air, several breaths may be required to inhale all of the medicament in inhaler (70). For example, inhaler (70) which is shown in FIG. 5A is similar to the inhaler shown in FIG. 4D. Accordingly, inhaler (70) has a filter (76) located adjacent end (74) in addition, one way valve (88), which opens at sub-atmospheric pressure, is positioned adjacent end (72).

End (72) is sealed by stopper (78). Medicament (90) is generally represented as being located near or on filter (76). As discussed above, if inhaler (70) is manufactured according to the steps set out in FIGS. 4A–4D, the medicament will tend to accumulate near or adjacent filter (76).

In order to restrict the amount of air which may be drawn through inhaler (70) with any inhalation, inhaler (70) is provided with end member (92) positioned at end (74) of inhaler (70) and one or more by-pass valve (98). End member (92) seals end (74) of inhaler (70). End member (92) may be formed as an integral part of inhaler (70). End member (92) has longitudinally extending member (94) which is sealed by releasable seal (96). Similarly, bypass valve (98) is sealed by releasable seal (100).

Figure 5B:
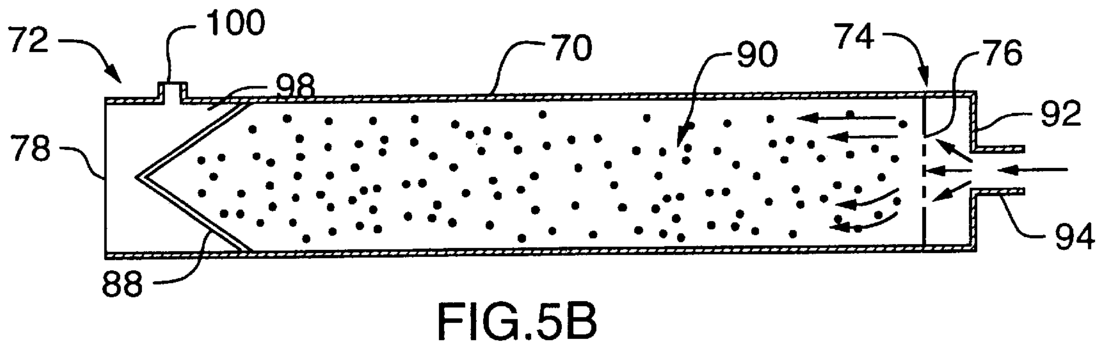
Figure 5C:
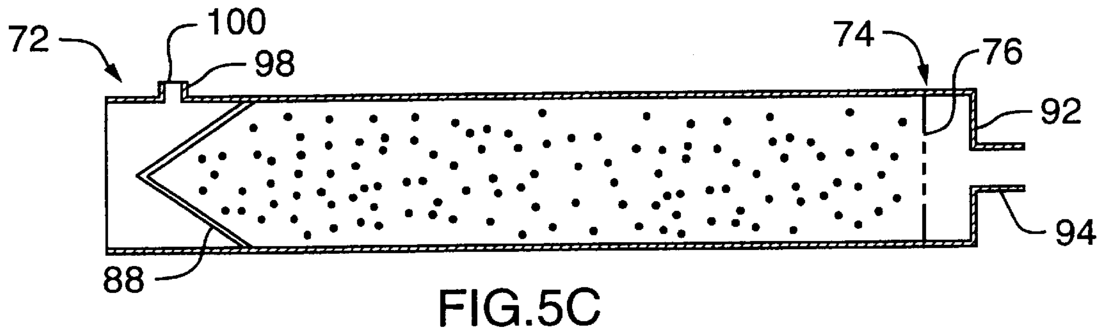
Figure 5D:
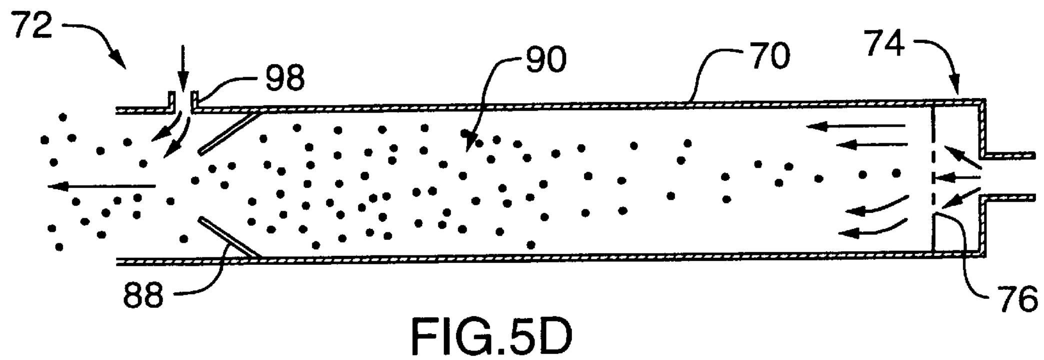

As discussed above, the medicament in inhaler (70) is preferably agitated so as to disperse medicament (90) throughout inhaler (70) prior to inhalation. One way to achieve this is to manufacture inhaler (78) to be at sub-atmospheric pressure. If this method is utilized, one of the releaseable seals may be removed thus allowing air to enter inhaler (70) as shown in FIG. 5B. The in rush of air disperses medicament (90) throughout inhaler (70). Subsequently, as shown in FIG. 5C, stopper (78) may be removed. Subsequently, as shown in FIG. 5D, releasable seal (100) may be removed. Thus, when the patient inhales, air is drawn through member (94), through inhaler (70) and through one way valve (88) into the airways of the patient. Simultaneously, air enters by-pass valve (98) thus diluting the concentration of medicament (90) in the air inhaled by the patient. Thus, more than one inhalation is required to withdraw all of the medicament from inhaler (70).

By varying the number and size of by-pass valves (98), as well as the size of member (94), the amount of air which flows through inhaler (70) as opposed to by-pass valve (98) may be adjusted thereby controlling the number of inhalations which may be required to withdraw all of the medicament from inhaler (70). Alternately, other modifications may be utilized to control the amount of medicament which is withdrawn from inhaler (70). For example, end member (92) may be replaced by a variable aperture which controls the amount of air which may pass through inhaler (70).

If the medicament in inhaler (70) is nicotine, inhaler (70) may be designed to look like a cigarette. In addition, by appropriately dimensioning by-pass valves (98) and member (94), inhaler (70) may contain an amount of nicotine which is contained in a cigarette. Several inhalations (i.e. puffs) would be required to withdraw all of the medicament in stages from inhaler (70). Thus, not only would the patient use inhaler (70) in the same manner as they would smoke a cigarette, but the transportation of nicotine into the patient and the absorbtion thereof in the lungs of the patient would more closely simulate smoking.

What is claimed is:

1. A method of assisting a person to withdraw from cigarette induced nicotine dependency by introducing a nicotine medicament into the lungs of a person using an inhaler comprising:

(a) a storage chamber for storing a mass of particulate medicament varying in size from about 0.1 μm to about 5 μm and comprising at least one nicotine formulation suitable for absorption into the bloodstream of the person through the alveoli and small airways of the person's lungs; and, (b) an air conduit to conduct air flow to the person, the air conduit sized to permit an air flow rate there through of up to about 1 L/s upon inhalation by the patient and including an air entrance and an air exit, the air entrance being open without any media containing a desiccant inhibiting the free flow air flow through the air entrance, the air conduit producing a turbulent flow of air there through upon inhalation by the person to entrain the medicament in the air inhaled by the person;

the method comprising:

(a) introducing a predetermined dose of the particulate medicament into the air conduit;

(b) creating an air flow through the air conduit responsive to the person inhaling through the inhaler;

(c) producing a cloud of particles suitable for absorption into the bloodstream of the person through the alveoli and small airways of the person's lungs by dispersing said medicament into the air passing through the air conduit, the turbulence of the air passing through the air conduit being sufficient to produce the cloud of particles; and, (d) withdrawing from the inhaler the cloud of particles together with air passing through the air conduit whereby on inhalation by the person, the medicament is introduced to the person's lungs for use by said person as a tobacco substitute.

2. A method as claimed in claim 1 wherein the predetermined dose is from about 0.1 to about 10 mg of nicotine.

3. A method as claimed in claim 1 wherein the predetermined dose is from about 0.2 to about 2 mg of nicotine.

4. A method as claimed in claim 1 wherein the predetermined dose is from about 0.1 to about 0.5 mg of nicotine.

5. A method as claimed in claim 1 wherein the individual medicament particles are in the size range of from about 0.1 to about 2 μm.

6. A method as claimed in claim 1 wherein the medicament additionally comprises a pharmaceutically acceptable carrier, excipient, or diluent.

7. A method as claimed in claim 1 wherein said inhaler has an air conduit which is sized to permit an air flow rate therethrough of up to about 0.5 L/s upon inhalation by the patient.

8. A method as claimed in claim 1 wherein said method is repeated at time intervals sufficient to reduce the negative effects of nicotine withdrawal.

9. A method as claimed in claim 1 and including the step, after introducing said medicament, of preventing said inhaler from introducing a further dosage of said medicament into said person's lung until a timed interval has elapsed.

10. A method as claimed in claim 1 wherein said air exit is open to permit the free flow of air therethrough.

11. A method of introducing a medicament into the lungs of a patient using a breath activated inhaler comprising an air conduit, a first opening and a second opening, said first opening and said second opening being releasably sealed, said air conduit sized to permit an air flow rate therethrough of up to about 1 L/s upon inhalation by the patient when said first and second seals are released, one of said first opening and said second opening being adapted to deliver the medicament to the mouth of the patient; and, a non-pressurized, particulate medicament comprising individual medicament particles and being suitable for absorption into the bloodstream of the patient through the alveoli and small airways of the patient's lungs positioned in said air conduit, said individual medicament particles varying in size from about 0.1 μm to about 5 μm, said method comprising the steps of:

(a) agitating said medicament in said air conduit to disperse said medicament in said air conduit;

(b) releasing said seals on said first and second openings; and (c) inhaling said medicament in the form of a cloud of particles entrained in air inhaled by the patient.

12. The method as claimed in claim 11 wherein said individual medicament particles vary in size from about 0.1 μm to about 2 μm.

13. The method as claimed in claim 11 wherein said individual medicament particles vary in size from about 0.1 μm to about 1 μm.

14. The method as claimed in claim 11 wherein, when said seals are removed, said air conduit is sized to permit an air flow rate therethrough of up to about 0.5 L/s upon inhalation by the patient.

15. The method as claimed in claim 11 wherein, the breath activated inhaler includes by-pass air feed means for supplying air to dilute the air passing through said air conduit so as to reduce the concentration of the medicament in the air which is inhaled by the patient.

16. The method as claimed in claim 15 wherein said by-pass air feed means is located near said one of said first opening and said second opening which is adapted to deliver the medicament to the mouth of the patient.

17. A method as claimed in claim 11 wherein said air exit is open to permit the free flow of air therethrough.

* * * * *